United States Patent
Maruyama et al.

(10) Patent No.: US 11,077,252 B2
(45) Date of Patent: Aug. 3, 2021

(54) DRUG CONTAINER

(71) Applicant: TERUMO KABUSHIKI KAISHA, Tokyo (JP)

(72) Inventors: Sayaka Maruyama, Sagamihara (JP); Yoshihiko Abe, Odawara (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 257 days.

(21) Appl. No.: 16/138,784

(22) Filed: Sep. 21, 2018

(65) Prior Publication Data

US 2019/0022325 A1    Jan. 24, 2019

Related U.S. Application Data

(63) Continuation of application No. PCT/JP2017/007542, filed on Feb. 27, 2017.

(30) Foreign Application Priority Data

Mar. 24, 2016  (JP) .............................. JP2016-060396

(51) Int. Cl.
| | |
|---|---|
| *A61M 5/31* | (2006.01) |
| *C08K 5/20* | (2006.01) |
| *A61J 1/03* | (2006.01) |
| *A61J 1/05* | (2006.01) |
| *A61K 38/00* | (2006.01) |
| *A61K 45/00* | (2006.01) |
| *C08K 5/101* | (2006.01) |
| *C08K 5/098* | (2006.01) |

(52) U.S. Cl.
CPC .............. *A61M 5/3134* (2013.01); *A61J 1/05* (2013.01); *A61K 38/00* (2013.01); *A61K 45/00* (2013.01); *A61M 5/31* (2013.01); *C08K 5/20* (2013.01); *A61M 2005/3131* (2013.01); *C08K 5/098* (2013.01); *C08K 5/101* (2013.01); *Y10T 428/1352* (2015.01)

(58) Field of Classification Search
CPC ............ A61M 2005/3131; A61M 5/31; A61M 5/3134; A61K 38/00; A61K 45/00; A61J 1/05; C08K 5/20; C08K 5/098; C08K 5/101; C08L 65/00
See application file for complete search history.

(56) References Cited

U.S. PATENT DOCUMENTS

| | | | |
|---|---|---|---|
| 5,945,187 | A | 8/1999 | Buch-Rasmussen et al. |
| 7,253,142 | B1 | 8/2007 | Suzuki et al. |
| 2010/0145284 | A1 | 6/2010 | Togashi |

FOREIGN PATENT DOCUMENTS

| | | |
|---|---|---|
| JP | H08-155007 A | 6/1996 |
| JP | 09-208731 A | 8/1997 |
| (Continued) | | |

OTHER PUBLICATIONS

Scheife et al, Stability of Intravenous Nitroglycerin Solutions, Journal of Pharmaceutical Science, 1982, vol. 71, No. 1.

(Continued)

*Primary Examiner* — Yan Lan
(74) *Attorney, Agent, or Firm* — Foley & Lardner LLP (57) ABSTRACT

A drug container includes a container body formed of a thermoplastic resin containing a cyclic polyolefin as a main component. The thermoplastic resin contains, as a lubricant, at least one compound selected from among a metal soap compound, an organic fatty acid ester compound, a synthetic wax compound, and a fatty acid amide compound. The lubricant content of the thermoplastic resin is 0.3 to 2.0 µg/g.

11 Claims, 7 Drawing Sheets

(56) References Cited

FOREIGN PATENT DOCUMENTS

| JP | 2001-506887 A | 5/2001 |
|---|---|---|
| JP | 2003-113112 A | 4/2003 |
| JP | 2006-321902 A | 11/2006 |
| JP | 2007-099767 A | 4/2007 |
| JP | 2010-155134 A | 7/2010 |
| JP | 2014-051502 A | 3/2014 |
| JP | 5555899 B2 | 6/2014 |
| JP | 2016-022145 A | 2/2016 |
| WO | WO-95/16565 A1 | 6/1995 |
| WO | WO-2007/132641 A | 11/2007 |

OTHER PUBLICATIONS

Hola, Eric T, Loss of nitroglycerin during microinfusion, American Journal of Hospital Pharmacy, 1984, vol. 41, pp. 142-144.

Ptachinski et al, Stability and availability of cyclosporine in 5% dextrose injection or 0.9% sodium chloride injection, American Journal of Hospital Pharmacy, 1986, vol. 43, pp. 43-47.

Kowaluk et al, Factors Affecting the Availability of Diazepam Stored in Plastic Bags and Administered through Intravenous Sets, American Journal of Hospital Pharmacy, 1983, vol. 40, pp. 417-423.

Kawano et al, Loss of Isosorbide Dinitrate or Nitoglycerin Solution Content in Practice Injection of Precision Continuous Drip Infusion, Journal of the Nippon Hospital Pharmacists Association. 1996, vol. 22, No. 2, pp. 167-172.

English Translation of the International Preliminary Report on Patentability in application No. PCT/JP2017/007542 dated Oct. 4, 2018.

Extended European Search Report dated Oct. 24, 2019 for corresponding Application No. 17769818.0 (7 pages).

International Search Report and Written Opinion in PCT/JP2017/007542, dated May 9, 2017, 9 pages.

DRUG CONTAINER

CROSS-REFERENCE TO RELATED APPLICATIONS

This is a bypass continuation of International Application No. PCT/JP2017/007542 filed on Feb. 27, 2017, which claims priority to Japanese Application No. 2016-060396 filed on Mar. 24, 2016. The contents of these applications are hereby incorporated by reference in their entirety.

BACKGROUND

The present disclosure relates to a drug container including a container body formed of a thermoplastic resin containing a cyclic polyolefin as a main component.

Conventionally, drug containers and syringe barrels are generally formed of glass, which is heavy and fragile. Therefore, plastic drug containers and plastic syringes have been developed and widely used instead of glass containers and syringes.

Such a plastic drug container may pose a problem in that the container adsorbs a drug and thus reduces the potency thereof. For example, it has already been reported that a pharmaceutical container or an infusion set often causes a reduction in the content of a highly lipophilic pharmaceutical (e.g., a nitroglycerin, cyclosporine, or benzodiazepine drug) contained therein. Thus, the interaction between an injection and a medical device causes problems (Journal of Pharmaceutical Science 71, 55-59, 1982, American Journal of Hospital Pharmacy 41, 142-144, 1984, American Journal of Hospital Pharmacy, 43, 94-97, 1986, American Journal of Hospital Pharmacy 40, 417-423, 1983, and Journal of the Nippon Hospital Pharmacists Association (Byoin Yakugaku) 22(2) 1996, 167-172.

Examples of the material for forming a drug container include polypropylene, polyethylene, cyclic olefin polymers, polyvinyl chloride, polyesters, polyamides, polycarbonates, and polymethacrylates. Cyclic polyolefins (i.e., the aforementioned cyclic olefin polymers) are less likely to cause the above-described drug adsorption and thus are useful as a material for forming a drug container. For example, JP 2016-22145 discloses a medical instrument (specifically, a prefilled syringe) formed of a cyclic polyolefin. JP 5555899 discloses a syringe formed of a cyclic polyolefin.

There has been proposed a container formed of a cyclic olefin polymer accommodating a protein solution formulation. For example, JP 2014-51502 discloses a container formed of a cyclic olefin polymer accommodating a recombinant protein having a sugar chain. JP 2001-506887 discloses a container formed of a cyclic olefin polymer accommodating an active drug (e.g., insulin or a human growth hormone). JP 2003-113112 discloses a container formed of a cyclic olefin polymer accommodating sterile calcitonin.

In the above case, the container for accommodating a protein solution formulation must be sterilized. Since a protein is coagulated or denatured by heating, a container accommodating a protein solution formulation cannot be subjected to heat sterilization (e.g., autoclave sterilization). Thus, in general, a container for accommodating a protein solution formulation is preliminarily sterilized, and the sterilized container is filled with an aseptically prepared protein solution formulation. Before charging of the formulation, the container is generally sterilized by irradiation with radioactive rays, such as gamma (γ)-rays or electron beams. Recently, attempts have been made to sterilize a drug-accommodating container by means of a gamma (γ)-ray or an electron beam.

SUMMARY

The drug container disclosed in, for example, JP 2016-22145 and JP 5555899 is produced through injection molding of a cyclic polyolefin. Thus, the material of the drug container, which contains a cyclic polyolefin as a main component, must further contain an additive for improving, for example, the moldability of the material and the stability of the drug container after production thereof.

The additive is, for example, a lubricant. Since the lubricant also serves as a mold release agent during injection molding of the drug container material, the lubricant is essential for production of the drug container. The lubricant is generally a metal soap compound, such as calcium stearate, zinc stearate, or zinc myristate. Although such a metal soap compound is effective as a lubricant, the compound may be eluted in a drug filled in the container; in particular, the compound is eluted in a large amount after sterilization of the container by means of electron beams. The eluted lubricant is highly likely to adversely affect the protein contained in a protein solution formulation filled in the container.

An object of certain embodiments described herein is to provide a drug container comprising a container body formed of a thermoplastic resin containing a cyclic polyolefin as a main component, which has good formability by injection molding and less elution of lubricant into drugs.

In one embodiment, a drug container comprising a container body formed of a thermoplastic resin containing a cyclic polyolefin as a main component, wherein the thermoplastic resin contains, as a lubricant, at least one compound selected from among a metal soap compound, an organic fatty acid ester compound, and a fatty acid amide compound, and has a lubricant content of 0.3 to 2.0 µg/g.

DETAILED DESCRIPTION

A drug container according to embodiments of the disclosure will be described with reference to the drawings.

A drug container includes a container body formed of a thermoplastic resin containing a cyclic polyolefin as a main component. The thermoplastic resin contains, as a lubricant, at least one compound selected from among a metal soap compound, an organic fatty acid ester compound, and a fatty acid amide compound, and the lubricant content of the thermoplastic resin is 0.3 to 2.0 µg (microgram)/g.

A synthetic resin-made syringe barrel based on the drug container of the present disclosure will now be described with reference to an embodiment illustrated in the drawings.

Figure 1:
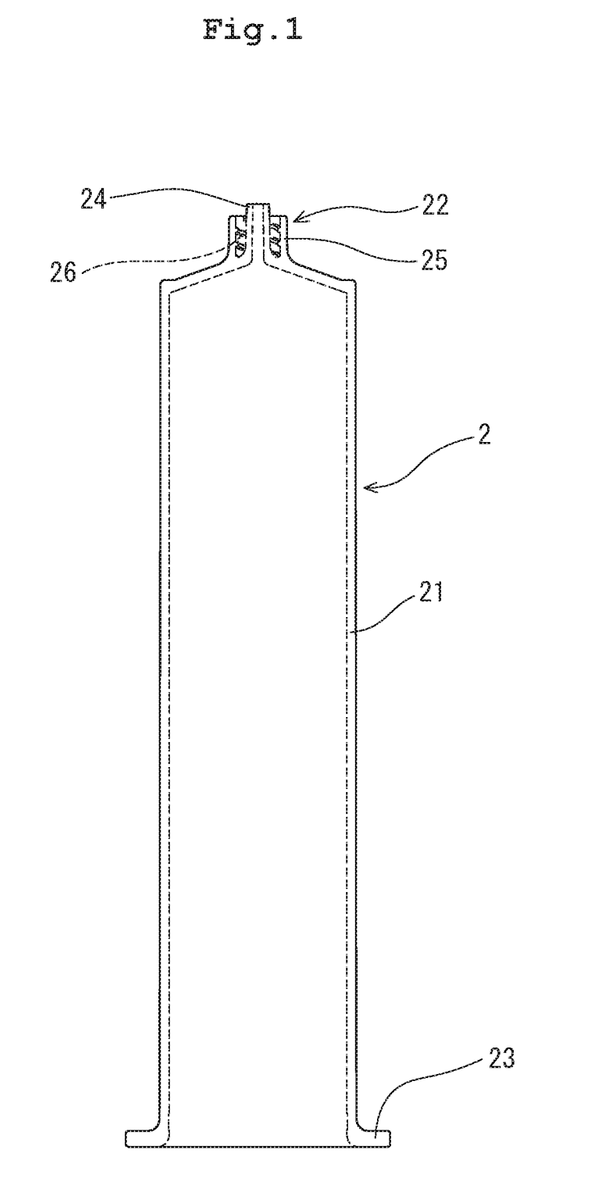
FIG. 1 is a front view of a synthetic resin-made syringe barrel based on the drug container of the present disclosure.
Figure 2:
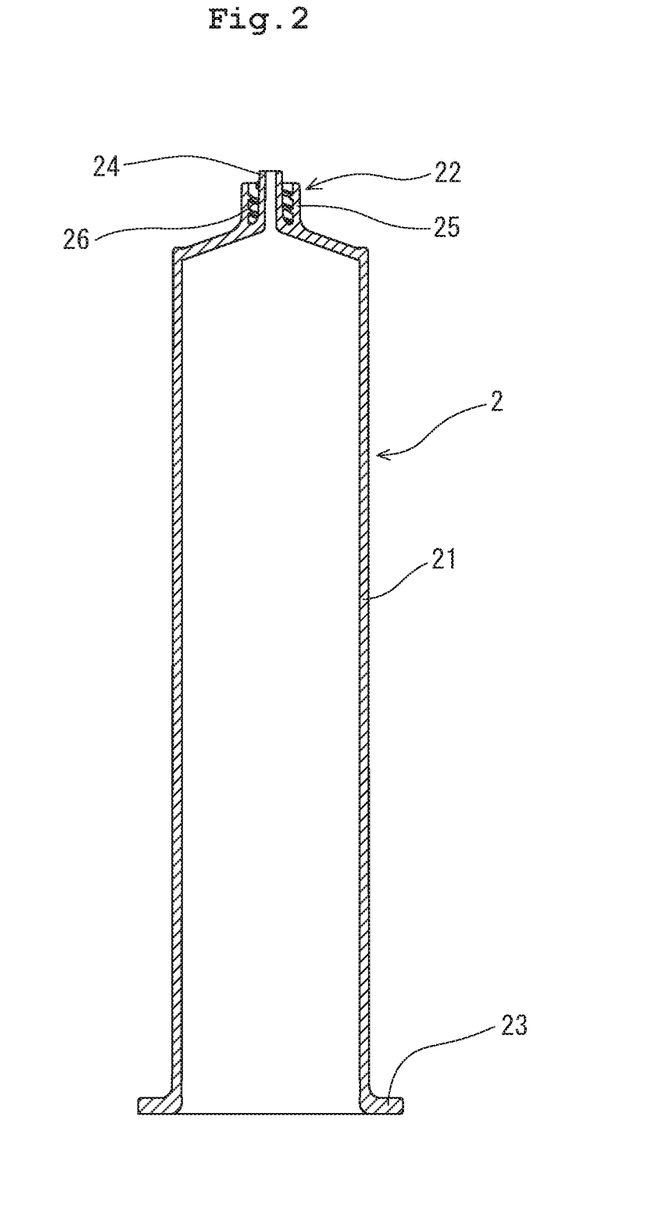
FIG. 2 is a vertical cross-sectional view of the synthetic resin-made syringe barrel of FIG. 1.

A syringe 1 according to the present embodiment includes a synthetic resin-made syringe barrel 2, which is an application of the drug container of the present disclosure formed of a thermoplastic resin containing a cyclic polyolefin as a main component; a gasket 4 slidable in the barrel 2; and a plunger 5 attached to the gasket 4.

The syringe barrel 2 according to the present embodiment has a barrel body 21, a nozzle 22 disposed at the front end of the barrel body 21, and a flange 23 disposed at the rear end of the barrel body 21 and extending outwardly.

The synthetic resin-made syringe barrel 2 of the present disclosure is formed of a thermoplastic resin containing a cyclic polyolefin as a main component. The cyclic polyolefin may be, for example, a copolymer formed from norbornene and an olefin (e.g., ethylene), a cycloolefin copolymer (COC); i.e., a copolymer formed from tetracyclododecene and an olefin (e.g., ethylene), a cycloolefin polymer (COP); i.e., a polymer formed through ring-opening polymerization of norbornene and subsequent hydrogenation, or a mixture thereof. Particularly preferred is, for example, a cycloolefin copolymer (COC) or a cycloolefin polymer (COP).

The thermoplastic resin containing a cyclic polyolefin as a main component further contains a lubricant. The lubricant is at least one compound selected from among a metal soap compound, an organic fatty acid ester compound, and a fatty acid amide compound.

The lubricant content of the thermoplastic resin is 0.3 to 2.0 µg/g. The lubricant content of the thermoplastic resin is particularly preferably 0.5 to 1.5 µg/g. The lubricant improves the surface smoothness of a molded product and serves as a mold release agent during injection molding. A lubricant content of less than 0.3 µg/g may result in an insufficient effect of the added lubricant.

The metal soap compound is preferably a fatty acid metal salt. Specifically, the metal soap lubricant is preferably a metal salt of a C12 to C30 fatty acid, such as calcium stearate, zinc stearate, magnesium stearate, zinc myristate, calcium hydroxystearate, calcium montanate, or zinc montanate. Particularly preferred are calcium stearate, zinc stearate, and zinc myristate. Still more preferred is calcium stearate.

The lubricant used in the present disclosure is at least one compound selected from among any of the aforementioned metal soap compound, an organic fatty acid ester compound, a synthetic wax compound, and a fatty acid amide compound. These lubricants may be used singly or in combination of two or more species. In the case where two or more lubricants are used, a metal soap compound or a fatty acid amide compound is preferably selected as a first lubricant. In the case where two or more lubricants are used, the amount of a metal soap compound or a fatty acid amide compound is preferably 30 to 90 wt. % relative to the total amount of the lubricants.

The organic fatty acid ester compound is, for example, a glycerin ester, polygrycerin ester, or sorbitol ester of a saturated or unsaturated fatty acid, or a polymer complex ester. Examples of the monovalent saturated or unsaturated fatty acid include capric acid, lauric acid, myristic acid, pentadecylic acid, palmitic acid, stearic acid, arachic acid, behenic acid, and montanic acid. Examples of the divalent saturated or unsaturated fatty acid include oleic acid, linoleic acid, linolenic acid, arachidonic acid, and erucic acid. Specific examples of the organic fatty acid ester compound include butyl stearate, monoglyceride stearate, pentaerythritol tetrastearate, hydrogenated castor oil, stearyl stearate, montanic acid ethylene glycol ester, montanic acid glycerin ester, montanic acid pentaerythritol ester, and calcium-containing montanic acid ester. The organic fatty acid ester compound is particularly preferably, for example, a partially saponified montanic acid ester or a polymer complex ester.

Examples of the fatty acid amide compound include lauramide, myristamide, palmitamide, stearamide, behenamide, oxystearamide, oleamide, linoleamide, ricinoleamide, ethylenebisstearamide, methylenebisstearamide, methylenebisstearobehenamide, ethylenebisoleamide, methylenebisoleamide, and erucamide. Of these, more preferred are, for example, oleamide, erucamide, and stearamide. As the lubricant, only erucamide or stearamide is preferable.

Specific examples of the lubricant (other than the metal soap compound) include Licowax OP (product of Clariant Japan K.K., partially saponified montanic acid ester), Loxiol G-78 (product of Cognis Japan Ltd., polymer complex ester), Licolub H-4 (product of Clariant Japan K.K., modified hydrocarbon wax), Loxiol VPN881 (product of Cognis Japan Ltd., mineral oil-based synthetic wax), Fatty Acid Amide S (product of Kao Corporation, fatty acid amide), Kao Wax EB-P (product of Kao Corporation, fatty acid amide), and Alflow HT-50 (product of NOF Corporation, fatty acid amide).

The synthetic resin (i.e., the material for forming the drug container of the present disclosure) may contain an additive, such as an antioxidant, a matting agent, a heat-resistant stabilizer, a weather-resistant stabilizer, an ultraviolet absorber, a plasticizer, a flame retardant, an antistatic agent, an anti-coloring agent, or a crystallization nucleating agent. Examples of usable antioxidants include phenolic antioxidants, phosphoric antioxidants, aromatic amine antioxidants, and hindered amine antioxidants.

The barrel 2 has the barrel body 21, the nozzle 22 disposed at the front end of the barrel body 21, and the flange 23 disposed at the rear end of the barrel body 21.

The barrel body has an approximately tubular shape and accommodates the gasket 4 in a liquid-tight and slidable manner. The nozzle has a tubular shape and has a diameter smaller than that of the barrel body 21. A front-end portion of the barrel body tapers toward the nozzle.

As illustrated in FIGS. 1 and 2, the flange 23 extends outwardly from the entire circumference of the rear end of the barrel body 21 and has an arc-like outer edge. In other words, the flange is in the form of a doughnut-shaped disk (i.e., a hollow disk).

As illustrated in FIGS. 1 and 2, the nozzle 22 has a nozzle body 24, and a collar 25 disposed concentrically with the nozzle body 24. The nozzle body 24 is disposed at the front end of the barrel 2. The nozzle body 24 has a front-end opening for discharging, for example, a drug solution from the barrel and tapers toward the front end. The collar 25, which has a cylindrical shape, is disposed concentrically with the nozzle 22 so as to surround the nozzle 22. The collar 25 is open at its front end, and each of the inner and outer diameters of the collar 25 is almost uniform from the base end to the front end. The front-end portion of the nozzle body 24 projects from the front-end opening of the collar 25. The front-end portions of the nozzle body 24 and the collar 25 are chamfered so that the nozzle body 24 and the collar 25 can be readily accommodated in a sealing member (sealing cap) 3.

The collar 25 has, on its inner peripheral surface, a thread groove (barrel-side screw-engagement portion) 26 for engagement with a rib formed on a nozzle accommodating portion of the sealing member (sealing cap) 3 described below or with a needle hub (not illustrated) to be connected when in use. Thus, the inner peripheral surface of the collar of the barrel 2 is engaged with the outer peripheral surface of the nozzle accommodating portion of the sealing cap 3. After removal of the sealing cap 3 from the barrel, a needle (needle hub) is attached to the thread groove (barrel-side screw-engagement portion) 26.

Figure 3:
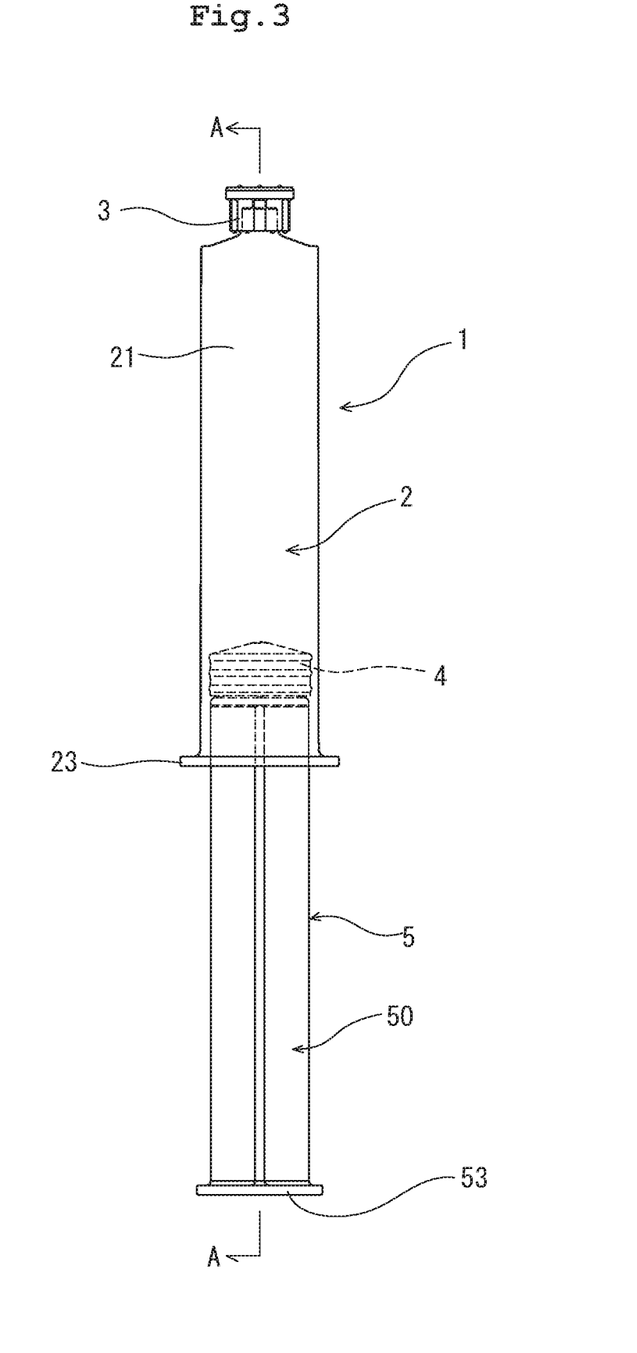
FIG. 3 is a front view of a prefilled syringe based on the drug container of the present disclosure.
Figure 4:
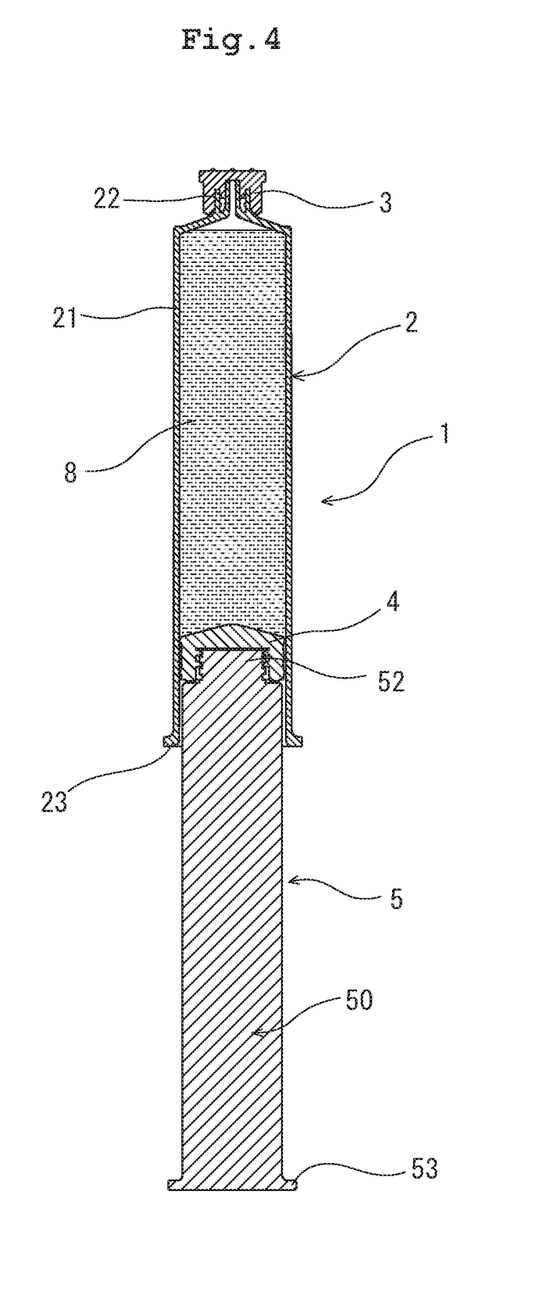
FIG. 4 is a cross-sectional view of the prefilled syringe taken along line A-A of FIG. 3.

As illustrated in FIGS. 3 and 4, the gasket 4 has a cylindrical body having an almost uniform outer diameter, and a tapered plugging portion extending from the cylindrical body toward the front end. The cylindrical body has, on its outer side surface, a plurality of annular ribs (three annular ribs in the present embodiment; the number of annular ribs can be appropriately determined (note: two or more), so long as liquid tightness and slidability are satisfied). These ribs come into contact with the inner surface of the barrel 2 in a liquid-tight manner. The plugging portion of the gasket 4 has a shape corresponding to that of the front-end inner surface of the barrel 2 so that little or no space is provided between the gasket 4 and the barrel 2 when the plugging portion butts against the front-end inner surface of the barrel 2.

The gasket 4 has, in its cylindrical body, a dent extending from the rear-end opening of the gasket toward the front end thereof. The dent can accommodate a front-end attachment portion 52 of the plunger 5. A gasket-side screw-engagement portion is provided on the surface of the dent (i.e., the inner surface of the cylindrical body). The gasket-side screw-engagement portion can be engaged with a plunger-side screw-engagement portion provided on the outer surface of the front-end attachment portion 52 of the plunger 5. The plunger 5 is not removed from the gasket 4 by engagement of these screw-engagement portions. The plunger 5 may be removed from the gasket 4 when not in use; i.e., the plunger 5 may be attached to the gasket 4 when in use. The lower end surface of the cylindrical body of the gasket 4 is provided with a plurality of ribs.

The material for forming the gasket 4 is preferably, for example, an elastic rubber (e.g., butyl rubber, latex rubber, or silicone rubber) or a synthetic resin (e.g., a styrenic elastomer, such as SBS elastomer or SEBS elastomer, or an olefinic elastomer, such as ethylene-α-olefin copolymer elastomer).

The plunger 5 has a plunger body 50 and the front-end attachment portion 52. The front-end attachment portion 52, which is attached to the gasket 4, projects from the plunger body 50 toward the front end. The plunger body 50 has a shaft having a cross-shaped cross section, and a pressing portion 53 disposed at the rear end of the shaft.

The shaft of the plunger body 50 is formed of four flat plates. A flange is disposed at the front end of the body 50 (shaft), and the disk-shaped plunger pressing portion 53 is disposed at the rear end of the body 50.

The front-end attachment portion 52 (i.e., protrusion) is disposed at the front end of the plunger 5. The front-end attachment portion 52 projects forward (toward the front end) from the vicinity of the center of the flange. The front-end attachment portion 52 preferably has a columnar or cylindrical shape.

The front-end attachment portion 52 has, on its outer surface, a plunger-side screw-engagement portion that is engaged with the gasket-side screw-engagement portion of the gasket 4. The plunger-side screw-engagement portion is provided with two spiral ribs so as to correspond to the spiral screw-engagement portion of the gasket 4. The plunger-side screw-engagement portion may be provided with only one spiral rib. In the syringe according to the present embodiment, the plunger 5 is attached to the gasket 4 by rotating the plunger 5 as described below.

The material for forming the plunger 5 is preferably a hard or semi-hard resin, such as high-density polyethylene, polypropylene, polystyrene, or polyethylene terephthalate.

The prefilled syringe 1 of the present disclosure includes the synthetic resin-made barrel 2 having an open front-end portion or an injection needle forming a front-end portion; the gasket 4 slidable in the barrel 2; the plunger 5 attached to the gasket 4; the sealing member 3 for sealing the open front-end portion of the synthetic resin-made barrel 2 or the injection needle; and a medical liquid filled in the barrel. The prefilled syringe 1 is autoclave sterilized. The synthetic resin-made barrel 2 is formed of a thermoplastic resin containing any of the aforementioned cyclic polyolefins as a main component and containing any of the aforementioned lubricants.

The barrel 2, the gasket 4, and the plunger 5 are those described above.

The medical liquid 8 filled in the prefilled syringe 1 of the present disclosure contains a medical substance that is susceptible to denaturation. The medical liquid containing a medical substance that is susceptible to denaturation is typically a protein solution formulation.

The protein solution formulation is preferably a solution formulation of a protein having bioactivity and used in the medical field. Specific examples of the protein solution formulation include solution formulations containing hematopoietic growth factors, such as erythropoietin, granulocyte colony-stimulating factor, granulocyte-macrophage colony-stimulating factor, and thrombopoietin; molecular target drugs, such as cytokine and monoclonal antibody; and proteins, such as serum albumin, tissue plasminogen activator, stem cell growth factor, interferon, and interleukin.

The conformation of the molecular target drug containing a protein (e.g., monoclonal antibody) is particularly important for exerting the pharmaceutical effects of the drug. Thus, the medical container of the present disclosure is particularly suitable as a container for accommodating a solution formulation containing a molecular target drug containing a protein having a methionine or cysteine residue in the amino acid sequence, such as abatacept, etanercept, adalimumab, rituximab, trastuzumab, or palivizumab.

No particular limitation is imposed on the components incorporated in the protein solution formulation accommodated in the medical container of the present disclosure, and the pH and other physical properties of the protein solution formulation. Conventionally used components and physical properties may be applied to the protein solution formulation, depending on the type of the protein solution formulation, for example.

The protein solution formulation accommodated in the medical container of the present disclosure may optionally contain one or more species selected from among a stabilizer, a buffer, a solubilizing agent, an isotonizing agent, a pH adjuster, a soothing agent, a reducing agent, an antioxidant, and other components.

Examples of the stabilizer that may be contained in the protein solution formulation include surfactants, such as nonionic surfactants (e.g., sorbitan fatty acid esters, glycerin fatty acid esters, polyglycerin fatty acid esters, polyoxyethylene sorbitan fatty acid esters, polyoxyethylene sorbitol fatty acid esters, polyoxyethylene glycerin fatty acid esters, polyethylene glycol fatty acid esters, polyoxyethylene alkyl ethers, polyoxyethylene polyoxypropylene alkyl ethers, polyoxyethylene alkyl phenyl ethers, polyoxyethylene hydrogenated castor oil, polyoxyethylene beeswax derivatives, polyoxyethylene lanolin derivatives, polyoxyethylene fatty acid amides, lecithin, glycerophospholipids, sphingophospholipids, and sucrose fatty acid esters) and anionic surfactants (e.g., alkyl sulfates, polyoxyethylene alkyl ether sulfates, and alkyl sulfosuccinic acid ester salts); and amino acids.

Of these, preferred are polyoxyethylene sorbitan fatty acid esters, and particularly preferred are polyoxyethylene sorbitan monooleate (Polysorbate 80) and/or polyoxyethylene sorbitan monolaurate (Polysorbate 20).

Specific examples of the amino acid that may be used as a stabilizer include leucine, tryptophan, serine, glutamic acid, arginine, histidine, lysine, methionine, phenylalanine, acetyl tryptophan, and salts thereof. The amino acid may be in an L-form, D-form, or DL-form.

Of these, preferred are L-leucine, L-tryptophan, L-glutamic acid, L-arginine, L-histidine, L-lysine, and salts thereof.

Examples of the buffer include phosphates, such as sodium monohydrogen phosphate and sodium dihydrogen phosphate; and citrates, such as sodium citrate.

Examples of the solubilizing agent include polyoxyethylene sorbitan monooleate (Polysorbate 80) and/or polyoxyethylene sorbitan monolaurate (Polysorbate 20), Cremophor, ethanol, and sodium dodecylbenzene sulfonate.

Examples of the isotonizing agent include polyethylene glycol; and saccharides, such as dextran, mannitol, sorbitol, inositol, glucose, fructose, lactose, xylose, mannose, maltose, sucrose, and raffinose.

No particular limitation is imposed on the protein content of the protein solution formulation accommodated in the medical container of the present disclosure. The protein content may be adjusted depending on, for example, the type of the protein, the intended use of the protein solution formulation, or the usage form of the protein solution formulation.

The medical liquid containing a medical substance that is susceptible to denaturation is not particularly limited to a protein solution formulation. The medical liquid may be, for example, a biopharmaceutical. The biopharmaceutical is, for example, a pharmaceutical produced by means of biotechnology, such as a cell culture technique or a gene recombination technique. Examples of the biopharmaceutical include protein pharmaceuticals, nucleic acid pharmaceuticals, and peptide pharmaceuticals.

Specific examples of the biopharmaceutical include, but are not particularly limited to, monoclonal antibodies, vaccines, interferon, insulin, growth hormone, erythropoietin, colony-stimulating factor, TPA, interleukin, blood coagulation factor VIII, blood coagulation factor IX, natriuretic hormone, somatomedin, glucagon, serum albumin, calcitonin, growth hormone-releasing factor, digestive enzymes, anti-inflammatory enzymes, antibiotics, antisense nucleic acids, antigen nucleic acids, decoy nucleic acids, aptamers, siRNA, microRNA, and biosimilars thereof.

In the prefilled syringe 1 according to the present embodiment, the barrel 2 has an open front-end portion, and the open front-end portion is sealed with the removably attached sealing member (sealing cap) 3. As illustrated in FIGS. 3 and 4, the sealing member (sealing cap) 3 has a closed end, a tubular body, and a nozzle accommodating portion formed in the tubular body. The nozzle accommodating portion has a portion for accommodating the front-end portion of the nozzle body 24 and a portion for accommodating the front-end portion of the collar 25.

The tubular body has a closed upper end and an open lower end. The nozzle accommodating portion accommodates almost the entirety of the nozzle 22. The nozzle accommodating portion has a short tubular portion disposed concentrically with the tubular body and extending downward (i.e., toward the opening) from the inner surface of the closed end. The short tubular portion has, at its lower end, a rib that can engage with the screw-engagement portion 26 formed on the inner surface of the collar 25.

The outer side surface of the cap is provided with an anti-slip protrusion. The upper surface of the closed end is provided with a plurality of ribs, and the lower surface of the tubular body is also provided with a plurality of ribs.

The material for forming the sealing member (sealing cap) is preferably an elastic material. Examples of the elastic material include natural rubber; synthetic rubbers, such as isoprene rubber, butyl rubber, butadiene rubber, fluororubber, and silicone rubber; and thermoplastic elastomers, such as olefinic elastomer and styrenic elastomer.

In all the aforementioned embodiments, the barrel 2 has a front-end opening. However, the barrel does not necessarily have such a structure. The barrel, the syringe, or the prefilled syringe may be in the form of a needle-attached barrel 30 as illustrated in FIGS. 7 and 8.

Figure 7:
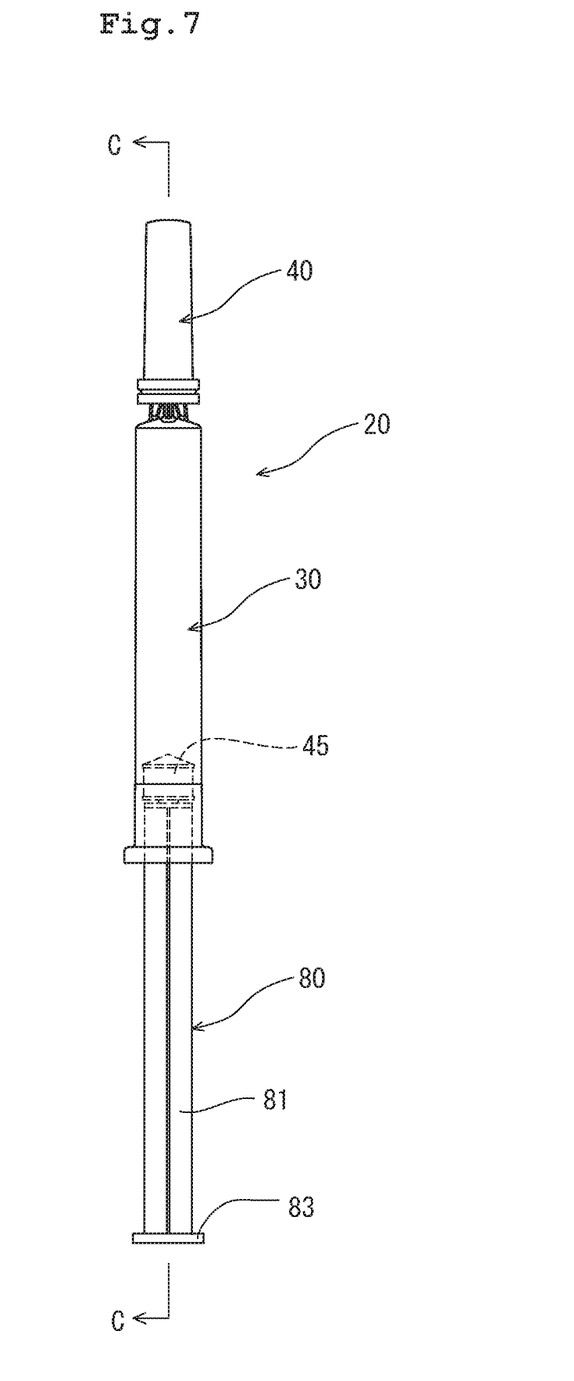
FIG. 7 is a front view of a prefilled syringe of another embodiment based on the drug container of the present disclosure.
Figure 8:
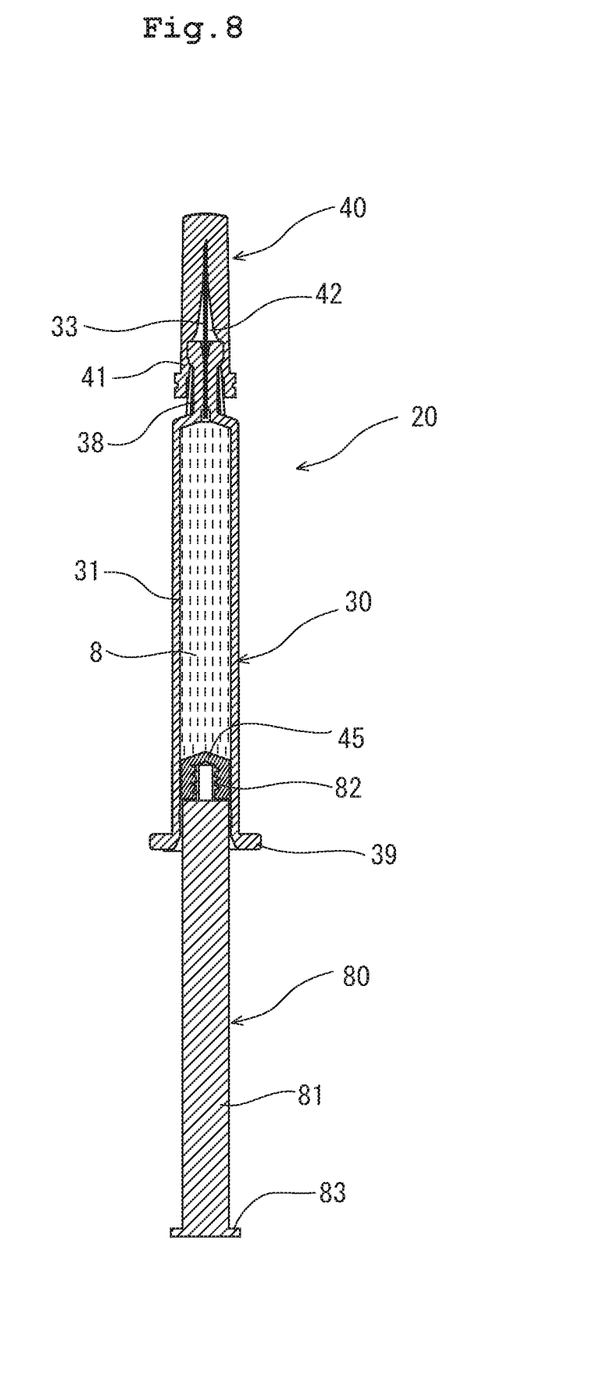
FIG. 8 is a cross-sectional view of the prefilled syringe taken along line C-C of FIG. 7.

A prefilled syringe 20 illustrated in FIGS. 7 and 8 includes a barrel 30 having a needle tube 33; a sealing member (cap) 40 attached to a front-end portion (needle) of the barrel 30; a gasket 45 disposed in the barrel 30 and slidable therein; a plunger 80 attached to the gasket 45; and the aforementioned medical liquid 8 filled in the barrel 30.

The needle tube 33 has an outer diameter of 0.41 to 0.18 mm. The needle tube 33 has an inner hole extending from the front end to the base end. The needle tube 33 has, at its front end, a tip that is punctured into a living organism. The needle tip has an acute-angled edge surface. The front-end portion (including the needle tip) of the needle tube 33 projects from the front end of a front-end portion 38 of the barrel 30. The needle tube 33 passes through a needle insertion hole, and the base end of the needle tube 33 reaches the interior of the barrel 30.

The material of the metal needle tube 33 is preferably, for example, stainless steel. However, the material is not limited to stainless steel, and may be another metal, such as aluminum, an aluminum alloy, titanium, or a titanium alloy. The needle tube 33 may be in the form of the aforementioned straight needle that meets ISO standards, or may be in the form of a partially tapered needle.

The barrel 30 has a body 31 in which the drug is filled, and a front-end portion 38 having a needle insertion hole. The body 31 has an approximately cylindrical shape and an accommodation portion therein. The body 31 has a flange 39 at its axial rear end.

The front-end portion 38 has a front-end bulging portion, and a tubular portion connecting the front-end bulging portion to the front end of the body 31. The front-end portion 38 has a needle insertion hole penetrating therethrough. The needle insertion hole is provided with the base end of the needle tube 33, which is integrated with the barrel by means of, for example, insert molding.

The cap 40 has a cylindrical shape. The axial base end of the cap 40 is open, and the axial front end thereof is closed. The cap 40 is formed of an elastic member (e.g., rubber or elastomer). The cap 40 is attached to the front-end portion 38 of the barrel 30 so as to cover the tip of the needle tube 33 and the front-end portion 38 of the barrel 30. As illustrated in FIG. 8, the needle tube 33 and the front-end portion 38 are inserted in an inner cavity 42 of the cap 40.

The diameter of the inner cavity of the cap 40 is almost equal to or slightly smaller than the outer diameter of the front-end bulging portion of the front-end portion 38. Thus, when the cap 40 is attached to the front-end portion 38, the outer peripheral surface of the front-end bulging portion comes into close contact with the inner peripheral surface of the cap 40. Therefore, the space surrounding the needle tube 33 projecting from the barrel 30 is hermetically sealed with the front-end bulging portion and the inner peripheral surface of the cap 40. This configuration can prevent contact of bacteria onto the needle tip.

A constricted portion of the front-end portion 38 at the boundary between the front-end bulging portion and a tapered fitting portion is tightened with an annular rib 41 provided on the inner peripheral surface of the cap 40 by means of the elastic force of the annular rib 41. Thus, the inner peripheral surface of the cap 40 is engaged with the constricted portion of the front-end portion 38. This can prevent removal of the cap 40 from the front-end portion 38 during conveyance of the prefilled syringe.

The plunger 80 has a body 81, a gasket attachment portion 82 provided at the front end of the body 81, and a pressing portion 83 provided at the base end of the body 81. The gasket has a plunger attachment portion that receives and engages with the gasket attachment portion 82 of the plunger 80.

In the present embodiment, the barrel 30 (except for the metal needle tube 33) is formed of any of the aforementioned synthetic resins.

A liquid-filled and sterilized synthetic resin-made container 10 based on the drug container of the present disclosure will next be described with reference to FIGS. 5 and 6. The liquid-filled and sterilized synthetic resin-made container 10 according to the present embodiment includes a synthetic resin-made container body 6, a sealing member 7 for sealing the opening of the container body, and a medical liquid 8 accommodated in the container body. The liquid-filled and sterilized synthetic resin-made container 10 of the present disclosure is preferably autoclave sterilized.

The synthetic resin-made container 10 includes the synthetic resin-made container body 6, the sealing member 7 for sealing the opening of the container body 6, and the medical liquid 8 accommodated in the container body.

As in the case of the aforementioned synthetic resin-made barrel 2, the container body 6 is formed of a thermoplastic resin containing a cyclic polyolefin as a main component and containing any of the aforementioned lubricants.

Specifically, the container body 6 is preferably formed of any of the materials for forming the synthetic resin-made barrel 2 described above. The accommodated medical liquid 8 is preferably the medical liquid 8 described in relation to the aforementioned prefilled syringe.

The drug-accommodated drug container 10 of the present disclosure includes the drug container body 6 having an opening, the sealing member (rubber closure in the present embodiment) 7 attached to the opening of the drug container body 6 for sealing the opening, and the medical liquid 8 accommodated in the drug container body 6.

The drug container body 6 may have any shape, so long as it has an opening and can accommodate the medical liquid 8 therein. The container body 6 according to the present embodiment has a cylindrical body portion 61 having a closed lower end, an opening 62 having a thick flange, and a neck portion 63 disposed between the opening 62 and the body portion 61 and having a diameter smaller than that of any other portion. The opening 62 and the neck portion 63 of the drug container body 6 serves as an accommodation portion that has a uniform inner diameter and accommodates a portion 72 of the rubber closure 7 that is fitted into the container (hereinafter the portion 72 will be referred to as "container fitting portion 72").

The container body 6 is preferably formed of any of the materials for forming the synthetic resin-made barrel 2 described above. The accommodated medical liquid 8 is preferably the medical liquid 8 described above in the prefilled syringe.

Figure 5:
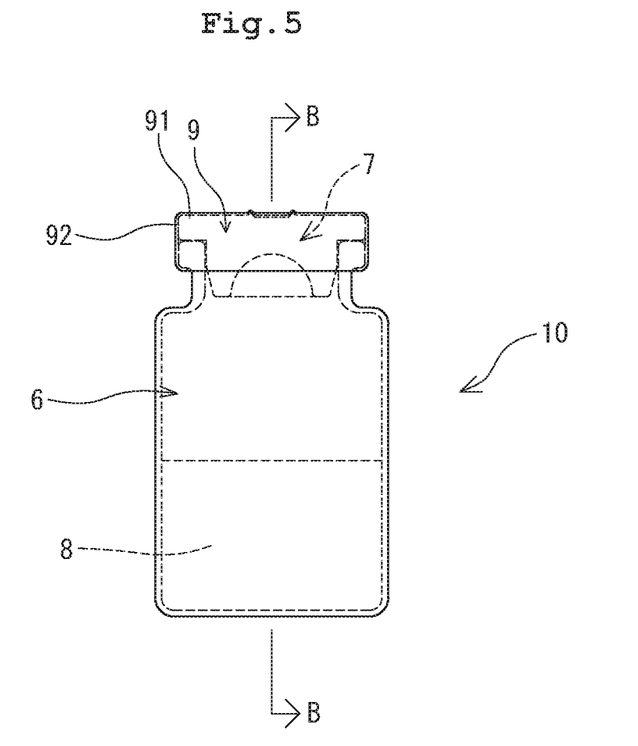
FIG. 5 is a front view of a liquid-filled and sterilized synthetic resin-made container based on the drug container of the present disclosure.
Figure 6:
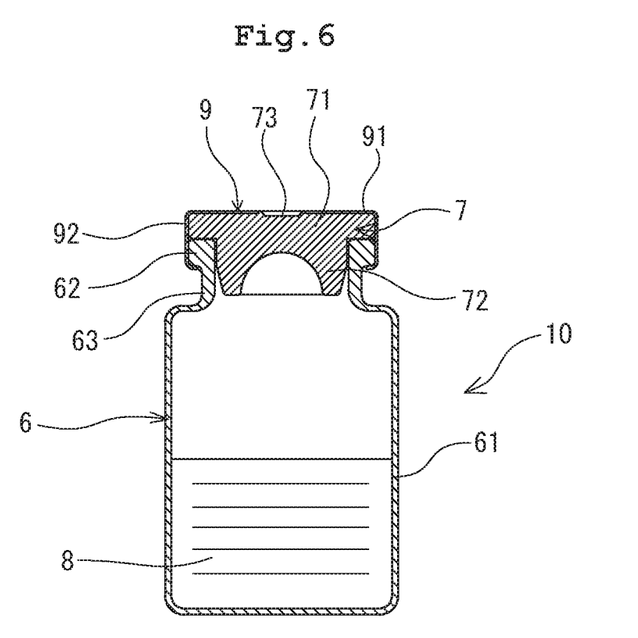
FIG. 6 is a cross-sectional view of the synthetic resin-made container taken along line B-B of FIG. 5.

As illustrated in FIGS. 5 and 6, the rubber closure 7 (i.e., a sealing member) has a disk-shaped body 71, and a container fitting portion 72 having an outer diameter smaller than that of the body 71 and extending downward from the center of the lower surface of the body 71. A peripheral portion of the lower surface of the body 71 serves as an annular contact portion that is in contact with the upper surface of the opening of the container body 6. The container fitting portion 72 has a tubular portion having an almost uniform outer diameter, and a tapered portion disposed at the lower end of the tubular portion. The outer peripheral surface of the fitting portion 72 is in contact with the inner peripheral surface of the opening 62 of the drug container body 6 to thereby achieve liquid tightness. The body 71 has, on its upper surface, an annular rib and a dent 73 provided in the annular rib.

The aforementioned shape of the rubber closure is merely an example. The rubber closure may have any shape, so long as it can seal the opening 62 of the drug container body 6 in a liquid-tight manner. The aforementioned rubber closure has the container fitting portion 72. However, the rubber closure does not necessarily have the container fitting portion 72, and may have a tubular portion that covers the outside of the opening 62 of the container body 6.

The rubber closure 7 is preferably formed of an elastic material. Examples of the elastic material include, but are not particularly limited to, rubber materials, such as natural rubber, isoprene rubber, butyl rubber, chloroprene rubber, nitrile-butadiene rubber, styrene-butadiene rubber, and silicone rubber (in particular, vulcanized rubber materials). Particularly preferred is diene rubber, since it exhibits elastic properties and can be subjected to γ-ray sterilization, electron beam sterilization, or autoclave sterilization.

The drug-accommodated drug container 10 according to the present embodiment includes a covering member 9 that is attached to the rubber closure 7 and covers a peripheral portion of the opening 62 of the drug container body 6 and a peripheral portion of the rubber closure 7. Preferably, the covering member 9 is formed of, for example, aluminum or heat-shrinkable film, and is in close contact with the rubber closure and the drug container body. The covering member 9 may cover the entire upper surface of the rubber closure 7, so long as a puncture needle (e.g., injection needle) can perforate through the covering member 9. In the present embodiment, the covering member 9 has an annular portion 92 and a thin disk-shaped upper surface portion 91. The lower end portion of the annular portion 92 covers the annular lower surface of the flange of the opening 62 of the container body 61.

The interior of the drug container 10 may be in a reduced pressure state.

EXAMPLES

Example 1

Erucamide (i.e., a fatty acid amide compound), serving as a lubricant, was added to a cyclic polyolefin [trade name:

ZEONEX 480, product of Zeon Corporation, glass transition temperature: 139 degree C., MFR: 20 g/10 min (280 degree C., load: 21 N)], to thereby prepare a cyclic polyolefin composition. The cyclic polyolefin composition was subjected to injection molding by means of a mold, to thereby form a barrel having a shape as illustrated in FIGS. 1 and 2. The total lubricant content of the cyclic polyolefin composition was 1.0 µg (microgram)/g. The resultant barrel was autoclave sterilized at 123 degree C. for 85 minutes.

Example 2

Erucamide (i.e., a fatty acid amide compound), serving as a lubricant, was added to a cyclic polyolefin [trade name: ZEONEX 480, product of Zeon Corporation, glass transition temperature: 139 degree C., MFR: 20 g/10 min (280 degree C., load: 21 N)], to thereby prepare a cyclic polyolefin composition. The cyclic polyolefin composition was subjected to injection molding by means of a mold, to thereby form a barrel having a shape as illustrated in FIGS. 1 and 2. The total lubricant content of the cyclic polyolefin composition was 0.5 µg/g. The resultant barrel was autoclave sterilized at 123 degree C. for 85 minutes.

Example 3

Erucamide (i.e., a fatty acid amide compound), serving as a lubricant, was added to a cyclic polyolefin [trade name: ZEONEX 480, product of Zeon Corporation, glass transition temperature: 139 degree C., MFR: 20 g/10 min (280 degree C., load: 21 N)], to thereby prepare a cyclic polyolefin composition. The cyclic polyolefin composition was subjected to injection molding by means of a mold, to thereby form a barrel having a shape as illustrated in FIGS. 1 and 2. The total lubricant content of the cyclic polyolefin composition was 1.5 µg/g. The resultant barrel was autoclave sterilized at 123 degree C. for 85 minutes.

Example 4

Calcium stearate (i.e., a metal soap compound), serving as a lubricant, was added to a cyclic polyolefin [trade name: ZEONEX 480, product of Zeon Corporation, glass transition temperature: 139 degree C., MFR: 20 g/10 min (280 degree C., load: 21 N)], to thereby prepare a cyclic polyolefin composition. The cyclic polyolefin composition was subjected to injection molding by means of a mold, to thereby form a barrel having a shape as illustrated in FIGS. 1 and 2. The total lubricant content of the cyclic polyolefin composition was 1.0 µg/g. The resultant barrel was autoclave sterilized at 123 degree C. for 85 minutes.

Comparative Example 1

Erucamide (i.e., a fatty acid amide compound), serving as a lubricant, was added to a cyclic polyolefin [trade name: ZEONEX 480, product of Zeon Corporation, glass transition temperature: 139 degree C., MFR: 20 g/10 min (280 degree C., load: 21 N)], to thereby prepare a cyclic polyolefin composition. The cyclic polyolefin composition was subjected to injection molding by means of a mold, to thereby form a barrel having a shape as illustrated in FIGS. 1 and 2. The total lubricant content of the cyclic polyolefin composition was 5.0 µg/g. The resultant barrel was autoclave sterilized at 123 degree C. for 85 minutes.

Comparative Example 2

Erucamide (i.e., a fatty acid amide compound), serving as a lubricant, was added to a cyclic polyolefin [trade name: ZEONEX 480, product of Zeon Corporation, glass transition temperature: 139 degree C., MFR: 20 g/10 min (280 degree C., load: 21 N)], to thereby prepare a cyclic polyolefin composition. The cyclic polyolefin composition was subjected to injection molding by means of a mold, to thereby form a barrel having a shape as illustrated in FIGS. 1 and 2. The total lubricant content of the cyclic polyolefin composition was 0.1 µg/g. The resultant barrel was autoclave sterilized at 123 degree C. for 85 minutes.

Referential Example 1

Erucamide (i.e., a fatty acid amide compound), serving as a lubricant, was added to a cyclic polyolefin [trade name: ZEONEX 480, product of Zeon Corporation, glass transition temperature: 139 degree C., MFR: 20 g/10 min (280 degree C., load: 21 N)], to thereby prepare a cyclic polyolefin composition. The cyclic polyolefin composition was subjected to injection molding by means of a mold, to thereby form a barrel having a shape as illustrated in FIGS. 1 and 2. The total lubricant content of the cyclic polyolefin composition was 1.0 µg/g. The resultant barrel was sterilized by irradiation with radioactive rays (25 kGy).

Experiment 1

Elution of nonvolatile organic compounds was examined by the method according to ISO 10993. Specifically, each of the barrels (10 g) of Examples 1 to 4, Comparative Examples 1 and 2, and Referential Example 1 was immersed in distilled water (100 mL) and then heated in an autoclave at 121 degree C. for one hour. Subsequently, the total amount of nonvolatile organic compounds in RO water was measured to thereby determine whether the total amount was 0.5 µg or less, relative to 1 g of the barrel. When the total amount was 0.5 µg or less, "Acceptable" was assigned, whereas when the total amount was more than 0.5 µg, "Unacceptable" was assigned. The results are shown in Table 1.

TABLE 1

|  | Results |
| --- | --- |
| Example 1 | Acceptable |
| Example 2 | Acceptable |
| Example 3 | Acceptable |
| Example 4 | Acceptable |
| Comparative Example 1 | Unacceptable |
| Comparative Example 2 | Acceptable |
| Referential Example 1 | Unacceptable |

Experiment 2

In each of Examples 1 to 4, Comparative Examples 1 and 2, and Referential Example 1, the mold releasability of the barrel from a mold cavity was determined during injection molding. When the resin remained in the mold cavity during release of the barrel from the mold, "Unacceptable" was assigned, whereas when no resin remained in the mold cavity during release of the barrel from the mold, "Acceptable" was assigned. The results are shown in Table 2.

TABLE 2

|  | Results |
| --- | --- |
| Example 1 | Acceptable |
| Example 2 | Acceptable |

TABLE 2-continued

| | Results |
|---|---|
| Example 3 | Acceptable |
| Example 4 | Acceptable |
| Comparative Example 1 | Acceptable |
| Comparative Example 2 | Unacceptable |
| Referential Example 1 | Acceptable |

The drug container of the present disclosure is as follows.

(1) A drug container comprising a container body formed of a thermoplastic resin containing a cyclic polyolefin as a main component, the drug container being characterized in that:

the thermoplastic resin contains, as a lubricant, at least one compound selected from among a metal soap compound, an organic fatty acid ester compound, and a fatty acid amide compound, and has a lubricant content of 0.3 to 2.0 µg/g.

In the drug container, the lubricant content of the lubricant-containing thermoplastic resin is 0.3 to 2.0 µg/g. Thus, the drug container exhibits good moldability for injection molding, and the lubricant is less likely to be eluted in a drug to be accommodated in the container. Even when the drug container accommodates a protein solution formulation therein, the protein is less affected by an eluted lubricant.

The aforementioned drug container may be embodied as follows.

(2) A drug container as described in (1) above, wherein the drug container is autoclave sterilized.

(3) A drug container as described in (1) or (2) above, wherein the thermoplastic resin contains the metal soap compound, and the metal soap compound is calcium stearate, zinc stearate, or zinc myristate.

(4) A drug container as described in any of (1) to (3) above, wherein the thermoplastic resin contains the organic fatty acid ester compound, and the organic fatty acid ester compound is a partially saponified montanic acid ester or a polymer complex ester.

(5) A drug container as described in any of (1) to (4) above, wherein the thermoplastic resin contains the fatty acid amide compound, and the fatty acid amide compound is at least one compound selected from among lauramide, myristamide, palmitamide, stearamide, behenamide, oleamide, erucamide, ethylenebisstearamide, ethylenebisbehenamide, ethylenebisoleamide, and ethylenebiserucamide.

(6) A drug container as described in (1) or (2), wherein the thermoplastic resin contains, as a lubricant, at least a metal soap compound or a fatty acid amide compound, and the amount of the metal soap compound or the fatty acid amide compound is 30 to 90 wt. % relative to the total amount of the lubricant.

(7) A drug container as described in any of (1) to (6) above, wherein the drug container comprises a syringe barrel forming the container body, a gasket disposed in the syringe barrel, and a sealing member that seals a front-end portion of the syringe barrel.

(8) A drug container as described in any of (1) to (7), wherein the drug container comprises the container body, and a sealing member that seals an opening of the container body.

(9) A drug container as described in any of (1) to (8), wherein the drug container comprises a medical liquid filled in the container body.

(10) A drug container as described in any of (1) to (9), wherein the drug container comprises a medical liquid filled in the container body, and is autoclave sterilized.

(11) A drug container as described in (9) or (10), wherein the medical liquid is a drug.

(12) A drug container as described in (11), wherein the drug is a protein solution formulation.

The invention claimed is:

1. A drug container comprising a container body formed of a thermoplastic resin containing a cyclic polyolefin as a main component,
wherein said thermoplastic resin contains, as a lubricant, a fatty acid amide compound,
wherein a lubricant content of said thermoplastic resin is 0.3 to 2.0 µg/g, and
wherein said drug container is autoclave sterilized.

2. A drug container according to claim 1, wherein said fatty acid amide compound is at least one compound selected from among lauramide, myristamide, palmitamide, stearamide, behenamide, oleamide, erucamide, ethylenebisstearamide, ethylenebisbehenamide, ethylenebisoleamide, and ethylenebiserucamide.

3. A drug container according to claim 1, wherein said lubricant is erucamide or stearamide.

4. A drug container according to claim 1, wherein said lubricant contains at least erucamide, and the amount of said erucamide is 30 to 90 wt. % relative to the total amount of said lubricant.

5. A drug container according to claim 1, wherein said drug container comprises a syringe barrel forming said container body, a gasket disposed in said syringe barrel, and a sealing member that seals a front-end portion of said syringe barrel.

6. A drug container according to claim 1, wherein said drug container comprises said container body, and a sealing member that seals an opening of said container body.

7. A drug container according to claim 1, wherein said drug container comprises a medical liquid filled in said container body.

8. A drug container according to claim 7, wherein said medical liquid is a drug.

9. A drug container according to claim 8, wherein said drug is a protein solution formulation.

10. A drug container according to claim 1, wherein said drug container comprises a drug filled in said container body, wherein and said lubricant is erucamide or stearamide.

11. A drug container according to claim 1, wherein said lubricant content of said thermoplastic resin is 0.5 to 1.5 µg/g.

* * * * *